United States Patent
D'Aurora (10) Patent No.: US 7,410,807 B2
(45) Date of Patent: Aug. 12, 2008

(54) PREGNANCY AND SEX IDENTIFICATION TEST BASED ON SALIVA OR OTHER BODILY FLUIDS

(76) Inventor: Vito J. D'Aurora, P.O. Box 280, Bella Vista, CA (US) 96008

( * ) Notice: Subject to any disclaimer, the term of this patent is extended or adjusted under 35 U.S.C. 154(b) by 718 days.

(21) Appl. No.: 10/349,715

(22) Filed: Jan. 23, 2003

(65) Prior Publication Data

US 2003/0138971 A1    Jul. 24, 2003

Related U.S. Application Data

(63) Continuation-in-part of application No. 09/912,342, filed on Jul. 24, 2001, now abandoned.

(60) Provisional application No. 60/220,279, filed on Jul. 24, 2000.

(51) Int. Cl.
   *G01N 33/53* (2006.01)

(52) U.S. Cl. ........................ 436/510; 435/7.1; 435/7.93; 436/518; 436/811; 436/814

(58) Field of Classification Search ................. 435/7.1, 435/7.92–7.95, 962, 970, 967; 436/518, 436/811, 814, 501, 524, 65, 510; 422/102, 422/104
   See application file for complete search history.

(56) References Cited

U.S. PATENT DOCUMENTS

| | | | | |
|---|---|---|---|---|
| 4,200,613 A | * | 4/1980 | Alfrey et al. | 422/71 |
| 4,454,235 A | * | 6/1984 | Johnson | 436/536 |
| 4,720,455 A | * | 1/1988 | Babu et al. | 435/7.93 |
| 4,842,995 A | * | 6/1989 | Iaccheri et al. | 435/5 |
| 4,891,321 A | * | 1/1990 | Hubscher | 422/57 |
| 5,063,151 A | * | 11/1991 | Kuehn et al. | 435/7.33 |
| 5,342,760 A | * | 8/1994 | Baker et al. | 435/7.92 |
| 5,888,834 A | * | 3/1999 | Ishikawa et al. | 436/518 |
| 5,916,815 A | * | 6/1999 | Lappe | 436/92 |
| 5,932,431 A | * | 8/1999 | Williams et al. | 435/7.93 |
| 6,027,943 A | * | 2/2000 | Kang et al. | 436/518 |
| 2003/0166518 A1 | * | 9/2003 | Beardslee et al. | 514/12 |

FOREIGN PATENT DOCUMENTS

GB    0125118    * 5/1984

* cited by examiner

*Primary Examiner*—Long V. Le
*Assistant Examiner*—Gary W Counts
(74) *Attorney, Agent, or Firm*—Sand & Sebolt (57) ABSTRACT

A method of testing an animal for pregnancy or sex identification comprising the steps of first, providing a first vessel containing a liquid and having a removable surface wherein said removable surface is at least partially coated with an antibody and then introducing a bodily fluid from the female animal into said first vessel so that said bodily fluid contacts the liquid and then manipulating the first vessel so that the liquid contacts the antibody. Then, a second vessel containing a reporter hormone solution is provided and the removable surface from the first vessel is displaced to the second vessel and manipulating the second vessel so that the reporter hormone solution contacts the removable surface. Then, a third vessel containing an indicating solution which has an appearance which is related to the amount of the reporter hormone contacted is provided, and the removable surface is displaced from the second vessel to the third vessel. The third vessel is manipulated so that the indicating solution contacts the removable surface. Then, a determination is made regarding the pregnancy or sex of the animal based on the appearance of the indicating solution.

23 Claims, 6 Drawing Sheets

STEP 5

FIG.13

PREGNANCY AND SEX IDENTIFICATION TEST BASED ON SALIVA OR OTHER BODILY FLUIDS

CROSS REFERENCE TO RELATED APPLICATIONS

This patent application is a continuation-in-part of U.S. patent application Ser. No. 09/912,342 filed Jul. 24, 2001, now abandoned, which claims priority from U.S. provisional patent application Ser. No. 60/220,279 filed Jul. 24, 2000; the disclosures of which are incorporated herein by reference.

BACKGROUND OF THE INVENTION

1. Technical Field

The present invention relates to molecular biology and microbiology and, more particularly, to pregnancy tests for mammals and sex determination in animals. Still more particularly, this invention relates to pregnancy tests for equine mammals which are based on saliva or other bodily fluids.

2. Background Information

The prior art discloses a number of ways to test for pregnancy in female mammals. U.S. Pat. No. 3,968,011 to Manantou, et al., for example, discloses a method for clorimetrically assaying the quantity of N-acetyl-.beta.-glucosaminidase in a female biological medium, such as saliva, which quantity is indicia of fertility or pregnancy. The implement is an absorbent material, such as paper strip, impregnated with a phenolic derivative of N-acetyl-.beta.-d-glucosamine that reacts in the presence of the glucosaminidase at an acide pH to form a phenol that has a distinct color at an alkaline pH, and a buffer that maintains said acid pH. The method may be carried out by wetting the implement with the medium, allowing the phenol to form, raising the pH to alkalinity by wetting the implement with an appropriate buffer solution, and comparing the color of the implement with a color standard.

U.S. Pat. No. 4,003,988 to Hoff, et al. discloses a direct agglutination reagent for pregnancy testing which comprises the use of suspensions of polystryrene latex particles sensitized with a globulin fraction of anti-serum to human chorionic gonadotropin (HCG). When mixed with urine or blood serum samples containing HCG, this reagent agglutinates indicating a positive test for pregnancy.

U.S. Pat. No. 4,123,504 to Banik, et al. discloses a method and device for detecting pregnancy. This test involves concentration by ultrafiltration of a sample of urine or serum from a subject; followed by determining the presence of human chorionic gonadotropin or of its .beta.-subunit in the concentrated sample.

U.S. Pat. No. 4,348,207 to Cappel discloses a method for testing for pregnancy in humans in which a sample of a patient's first morning urine is added to a test tube containing a known lyophilized reagent. The tube is capped, shaken to mix the contents, and placed upright for one to two hours. The tube is then inverted and compared with positive and negative standard vials to show either agglutination of particles, such as red blood cells contained therein, in which case the subject is not pregnant, or a failure to agglutinate, in which event the patient is pregnant. The test tube is of sufficient dimension to support capillary action and is formed from, or has its interior surface coated with, a material which is non-wettable to the liquid contained therein.

U.S. Pat. No. 4,716,123 to Wood discloses a home pregnancy test in which a specifically binding biomaterial is attached to a macroextensive surface of a plastic strip or the like. A biological substance which is a specific binding partner to a binding site of the specifically binding biomaterial is attached to each of a plurality of synthetic particles. The particles are of a preselected size, refractive index, or the like to enhance their visibility in accordance with the Mie scattering phenomenon. Testing is by either contacting the particles with the strips to obtain adherence of the particles to the strips, or by exposing strips having the particles already adhering to them to a solution containing either the specifically binding biomaterial or the biological substance, whereby the particles adherence to the strip is eliminated.

U.S. Pat. No. 4,720,455 to Babu, et al. discloses a progesterone concentration level test for mammalian body fluids particularly adapted for milk whereby estrus and pregnancy can be determined. The test can be carried out with a kit of several reagents, test tubes and a dip-stick carrying an anti-progesterone monoclonal antibody.

U.S. Pat. No. 5,837,197 to Porrazzo, et al. discloses a fertility analysis and reproductive health system that is applicable to both female and male mammals. The invention disclosed in this patent is a portable, handheld, integrated unit which can be manufactured out of plastic. The unit can be disposable for hygienic purposes, or cleaned or sterilized for repeated use as desired. Aspects of the invention include the following: an immediate testing methodology employing any and all female fluids or secretions called positive fertility testing; the creation of a plastic, completely integrated, portable, self-contained and self-focusing examination system which relies on a visual reference system making it language independent; a test area section with replaceable slides where different, specific wavelengths of light are employed; the embodiment of a compound test areas so that multiple positive fertility tests may be conducted simultaneously; implementing the ability to immediately perform two or more positive fertility tests simultaneously using different female fluids or secretions; providing a novel batter powered microprocessor system to automatically perform the positive fertility testing; providing an accurate indicator of positive ovulation whereby the woman may pinpoint times of greatest fertility, thereby knowing the optimum time period for achieving pregnancy.

The prior art also discloses possibly relevant art concerning methods of detecting ovulation in female mammals. U.S. Pat. No. 4,385,125 to Preti, et al., for example, discloses that the level of certain alcohols is dramatically increased during the ovulation cycle of mammals. This patent thus utilizes this change to precisely ascertain the time of ovulation by monitoring the concentration of alcohols noting that a spike in the concentration indicates a time of ovulation. While this device and process of this patent determines the alcohol level by measuring such alcohol levels in saliva, it does not utilize reporter enzymes to measure the level of certain hormones in saliva to determine pregnancy, but only to measure alcohol to determine ovulation.

U.S. Pat. No. 5,460,976 to O'Connor discloses a method of predicting ovulation and a test kit is described which allows one to accurately predict the time of ovulation in an animal in advance thus permitting the highest rate of pregnancy to be achieved and at the same time minimizing embryonic death.

U.S. Pat. No. 5,721,142 to Klemm, et al. also relates to a method of monitoring the mammalian reproductive cycles. In the method disclosed in this patent the quantity of one or more low molecular weight compounds such as acetal/dehyde are monitored.

U.S. Pat. No. 5,837,197 to Porrazzo, et al. discloses a positive fertility testing and reproductive health system. Inasmuch as this patent relates generally to the measurement of reproductive health and fertility status, it discloses a number of the general features of the invention including testing for enzymes in saliva to determine a male or female's reproductive state and health.

U.S. Pat. No. 5,914,271 to Law, et al., discloses a fertility test and more particularly, relates to the testing of magnesium and calcium concentrations in saliva. More specifically, within the three to five days immediately preceding ovulation, the calcium and magnesium concentrations in the saliva drop. As a result, concentration monitoring can be done by any conventional means for quantitatively analyzing the calcium and magnesium to determine the fertility state of the user.

A need still exists, however, for improved ways of testing for pregnancy in mammals.

Many species of avians as well as other animals also do not display phenotypic differences between the sexes, especially in immature individuals. With respect to avians, such sex identification may be difficult in some commercial species such as parrots and ratites, and for certain endangered species such as the California Condor and Whooping Crane as well as non-endangered species, such as the Canada Goose.

Gender identification can be performed in sexually monomorphic birds and other animals through surgical examination. Alternatively, sex identification can sometimes be made through karyotype analysis.

Another alternative method of sex identification in birds is disclosed in U.S. Pat. No. 5,679,514 to Baker. This method comprises the steps of obtaining a DNA sequence which includes the W specific chromosome from the bird. Then, there is the step of identifying the nucleotides of the DNA sequence of the W specific chromosome. This prior art method also pertains to a method of determining the sex of a bird, and a method of determining genetic relatedness between two birds.

The above described methods of sex identification may, however, be relatively expensive and time consuming. A need, therefore, exists for an improved method of sex identification for monomorphic avians and other animals.

SUMMARY OF THE INVENTION

It is an object of the present invention to provide an accurate, easy and inexpensive means for detecting pregnancy in equines or other mammals and for identifying sex in monomorphic avians and other animals.

It is another object of the present invention to provide a test for pregnancy in equines or other mammals or for sex identification in monomorphic avians and other animals which can be performed at home and without laboratory facilities and without specialized veterinary or medical training.

It is another object of the present invention to provide a test for pregnancy in equines and other animals and for sex identification in monomorphic avians and other animals which is sensitive enough to allow use of saliva as the bodily fluid.

It is still another object of the present invention to provide a test for pregnancy in equines and other animals and for sex identification in monomorphic avians and other animals which has a low level of ambiguity and a high level of reliability.

It is still another object of the present invention to provide a test for pregnancy in equines and other mammals and for sex identification in monomorphic avians and other animals which provides the ability to provide prompt test results to the user.

Another object of the present invention is to provide a simple and easy to use kit by means of which tests for pregnancy in equines or other mammals or for sex identification in monomorphic avians and other animals may be performed at home or on a farm or ranch by individuals without specialized veterinary or medical training.

These and other objects are met by the present invention which is a method of testing a female mammal for pregnancy or identifying the sex of an animal comprising the steps of first providing a first liquid medium and then introducing a bodily fluid from the female animal into said liquid and then providing a solid surface supporting an antibody and contacting said liquid with the solid surface supporting the antibody. Then a reporter hormone solution is provided and the solid surface supporting the antibody is displaced to place said solid surface supporting the antibody in contact with the reporter hormone solution. Then the solid surface supporting the antibody is contacted with an indicating solution. A determination is then made regarding pregnancy or sex of the animal based on the appearance of either the solid surface supporting the antibody or the indicating solution. It is found that the use of the reporter solution in a separate step makes the test more sensitive so as to facilitate the use of the test with saliva.

The present invention also encompasses a method of testing a female mammal for pregnancy or identifying the sex of animal comprising the steps first providing a first liquid medium, a reporter hormone solution, a solid surface supporting an antibody and then adding to said first liquid medium either before or after adding the reporter hormone, a bodily fluid from said female mammal. The female animal is a member of a species of animal and for that species of animal there is a known concentration of an indicating hormone present in the bodily fluid that varies during pregnancy. The amount of antibody on the solid surface is titrated to give the most sensitivity between the presence and absence of indicating hormone for said species. After the addition of both the reporter hormone and the bodily fluid to the first liquid medium, the first liquid medium is contacted with the solid surface supporting the antibody. The solid surface supporting the antibody with various levels of reporting hormone depending on the native hormone in the bodily fluid, is contacted with an indicating solution. A determination is then made regarding the pregnancy of the female animal or sex of the animal based on the level of color on either the solid surface supporting the antibody or the indicating solution, depending on the reporting solution used. It is found that ambiguity of the test is reduced when the amount of antibody on the solid surface is titrated precisely to the minimum concentration required yet high enough to produce sufficient color.

The present invention also encompasses a method of testing a female mammal for pregnancy or identifying the sex of an animal comprising the steps of first, providing a first vessel containing a liquid and having a removable surface wherein said removable surface is at least partially coated with an antibody and then introducing a bodily fluid from the female animal into said first vessel so that said bodily fluid contacts the liquid and then manipulating the first vessel so that the liquid contacts the antibody. Then, a second vessel containing a reporter hormone solution is provided and the removable surface from the first vessel is displaced to the second vessel and manipulating the second vessel so that the reporter hormone solution contacts the removable surface. Any antibody not containing hormone from the bodily fluid will then bind the reporter hormone. Then, a third vessel containing an indicating solution which has an appearance which is related to the amount of the reporter hormone contacted is provided, and the removable surface is displaced from the second vessel to the third vessel. The third vessel is manipulated so that the indicating solution contacts the removable surface. Then, a determination is made regarding the pregnancy of the female or sex of the animal based on the appearance of the indicating solution in the vessel or intensity of color on the removable surface where the antibody and reporter hormone are attached.

The invention also encompasses a method of testing a female mammal for pregnancy or identifying the sex of an animal comprising the steps of providing a first vial containing a buffer liquid and having a removable cap having an inner surface which is at least partially overlaid with a solid phase antibody coating. A bodily fluid from the female animal is then introduced into said first vial so that said bodily fluid contacts said buffer liquid and the first vial is then manipulated so that the buffer liquid contacts the solid phase antibody coating on the inner surface of the cap. A second vial containing a reporter hormone is then provided, and the cap is removed from the first vial to said second vial, and the second vial is then manipulated so that the reporter hormone solution contacts the solid phase antibody coating on the inner surface of the cap. A third vial is provided which has an indicating solution which has an appearance which is related to the amount of reporter hormone contacted. The cap is removed from the second vial to said third vial, and the third vial is manipulated so that the indicating solution contacts the solid phase antibody coating on the inner surface of the cap. A determination regarding the pregnancy of the female animal or sex of the animal based on the appearance of the indicating solution in the vial or intensity of color on the removable cap where the antibody and reporter hormone are attached.

The invention also encompasses a kit for use in testing a female animal for pregnancy or identifying the sex of an animal which includes a first viall containing a liquid buffer and having an opening and a removable cap adapted to close said opening and having an inner surface which is at least partially overlaid with a solid phase antibody coating. There is also a second vial containing a reporter hormone solution and having an opening which is adapted to being closed by the removable cap. Also included in the kit is a third vial containing an indicating solution and having an opening which is adapted to being closed by the removable cap.

The number of vials may vary depending on the specific hormones of interest, the species-specific hormones and their characteristics, the reporter hormones chosen, or other components of the test. Each component can influence the necessary steps to optimize the invention. With respect to the test for determining the sex of animals, in some animals visual observations are insufficient to determine whether the animal is male or female. For example, this test would be able to determine the sex of birds and reptiles, whose genitalia are not visible without significant manipulation of the animal. For instance, estrogen and it's derivatives are found in significantly higher levels in female animals than in male animals. Other hormones also have a significant differential concentration between the male and female members of an animal species. Testing for these hormones would enable one to determine the sex of the animal. The list of hormones and animals is prohibitively large for this application, but is well known from numerous literature references.

BRIEF DESCRIPTION OF THE DRAWINGS

The preferred embodiment of the invention, illustrative of the best mode in which applicant contemplated applying the principles, is set forth in the following description and is shown in the drawings and is particularly and distinctly pointed out and set forth in the appended claims.

FIGS. 1a-7 show a kit by means of which the method of the present invention may be carried out, wherein

FIG. 1b is a cross section through 1b-1b in FIG. 1a;

DESCRIPTION OF THE PREFERRED EMBODIMENTS

Figure 1A:
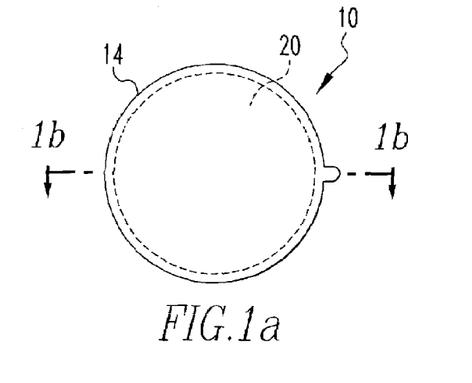
FIG. 1a is a bottom plan view of a solid phase antibody cap section of a preferred embodiment of the kit of the present invention in which the protective foil cover of this cap is in place.
Figure 1B:
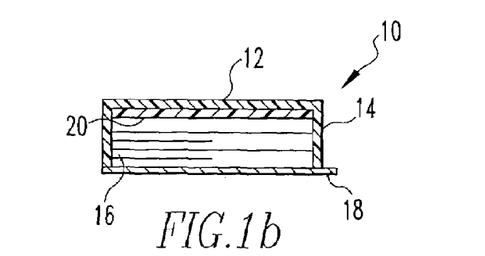
Figure 1C:
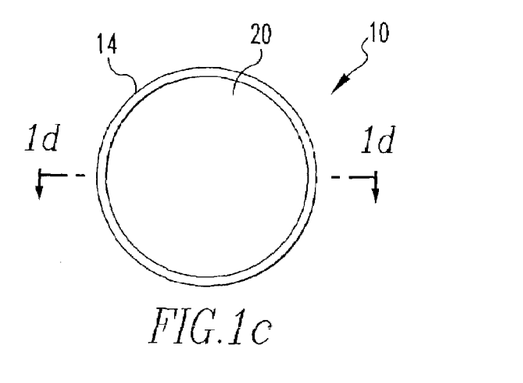
FIG. 1c is a bottom plan view of a solid phase antibody cap section shown in FIG. 1a in which the protective foil cover has been removed.
Figure 1D:
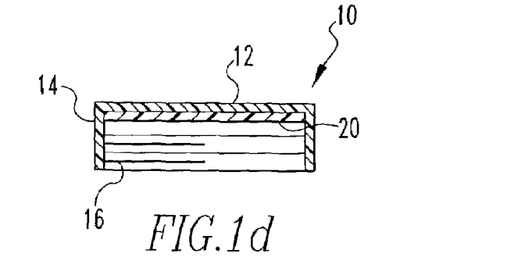
FIG. 1d is a cross section through 1d-1d in FIG. 1c.

Referring particularly to FIGS. 1a-7, a kit which may be used in the method of the present invention is shown. This kit includes a solid phase antibody cap section which is shown in FIGS. 1a-1d generally at numeral 10. This cap has a top 12 and a sidewall 14 having an inner thread 16. At the base of the sidewall there is a foil protective cover 18 as is shown in FIGS. 1a and 1b which may be removed as is shown in FIGS. 11c and 1d. On the inner side of the top 12 there is a solid phase antibody layer 20. This solid phase antibody layer is a layer or layers of proteins, including the antibody and possibly other enhancing proteins and include various antibodies and various other enhancing proteins and processes. The solid phase may be any material that has a natural irreversible affinity for proteins. Non-limiting examples include nitrocellulose paper, diatomaceous earth coated onto a surface, and plastics. The solid phase material may also be any material that is chemically reactive to proteins where on proteins can be chemically attached to the material. Non-limiting examples include plastics, paper materials, and polymers. The antibodies can be any monoclonal or polyclonal antibody to any hormone or combination of hormones that are indicative of pregnancy or whose levels increase or decrease during pregnancy, and examples of which include antibodies directed against progesterone, estrogen, follicle stimulating hormone, leutinizing hormone, other steroid hormones or their derivatives or metabolites, and other protein hormones or their derivatives or metabolites. Antibodies may also be any antibody listed above from any species that cross reacts sufficiently between species to be used to detect pregnancy in a different species than the originating species of the antigen. Enhancing proteins and processes include artificial antibodies generated by various processes. Non-limiting examples include proteins that are not antibodies but have similar affinities for any hormones listed above, and antibodies that are manufactured from parts of multiple antibodies, such as the combination of more than one antibody reactive site into a single protein body that functions like an antibody. Multiple layers of proteins laid down on any surface in (1a) that are designed to enhance the sensitivity of the system, reduce non-specific binding, and increase the stability of the antibody coating. Antibody levels on the solid phase can be adjusted to increase or decrease the sensitivity of the assay. As an example, equine levels of progesterone in saliva vary with the state of pregnancy. Within days of the start of gestation, the levels of progesterone increase. Measuring the presence of progesterone in saliva is indicative of pregnancy. Solid phase antibody consists of an anti-progesterone polyclonal antibody against progesterone on a nitrocellulose paper (solid phase) creating a "spot" of antibody. The liquid antibody solution is applied to a very small area of the solid phase using a small pipette. To get the proper amount of antibody on the solid phase, multiple applications can be made. This is done by applying the antibody solution and letting it dry and repeating the process until the proper amount of antibody is absorbed onto the solid phase, without spreading the antibody spot by applying a large amount of antibody solution in one applications. The amount of antibody that gives the most sensitive assay is determined by creating several test solid phase spots with differing amounts of antibody and testing the solid phase with saliva from mares of various states of pregnancy to determine that level of antibody that distinguishes the various states best. The solid phase with the correct level of antibody in the spot is put into the cap or strip (depending on the method used to perform the assay), as described in the figures, and is used for the assay as described. An alternative to the development of color on the solid phase spot, the assay can be designed so that a solution generates a color change that is indicative of the state of pregnancy.

Figure 2:
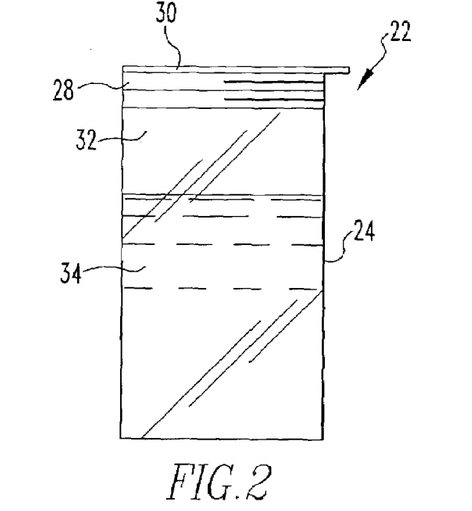
FIG. 2 is a front elevational view of the first vial section of a preferred embodiment of the kit of the present invention.

Another element of the kit of the present invention is a first vial which is shown in FIG. 2 generally at numeral 22. This vial is cylindrical in shape, has a sidewall 24. There is a thread 28 on the outside of sidewall 24 for engagement with the thread 16 on the cap 10. The first vial 22 has a temporary foil protective cover 30 which may be removed at the time of the test as is described hereafter to provide an open top 32. Inside the first vial 22 there is a liquid buffer solution 34 which may be any buffer in which the antibody, hormone, and solid phase are stable. The buffer will contain an antimicrobial component to inhibit spoilage. The buffer may also contain a surfactant or detergent that could help to minimize non-specific binding of assay components to any physical surface. Non-limiting examples include buffering components such as TRISMA buffer with a pH near 7; or phosphate buffered saline, consisting of various ortho phosphate salts in a sodium chloride saline solution to achieve a pH near 7. The buffer may also be antimicrobial such as sodium azide and thimerosol. The buffer may also be detergent/surfactants such as TWEEN-20, TWEEN-80, or sodium dodecylsulfate. Buffering components, antimicrobials and detergents/surfactants are chosen based on the other components of the assay kit. As will be appreciated by those skilled in the art, certain reporter enzymes, chromophores, and hormones are more stable in certain combinations of buffer components.

Figure 3:
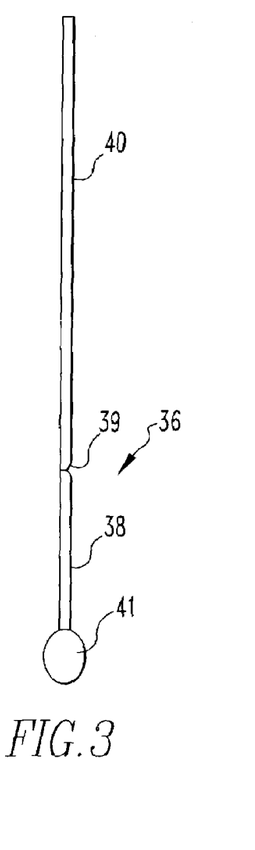
FIG. 3 is a front elevational view of the swab section of a preferred embodiment of the kit of the present invention.
Figure 4:
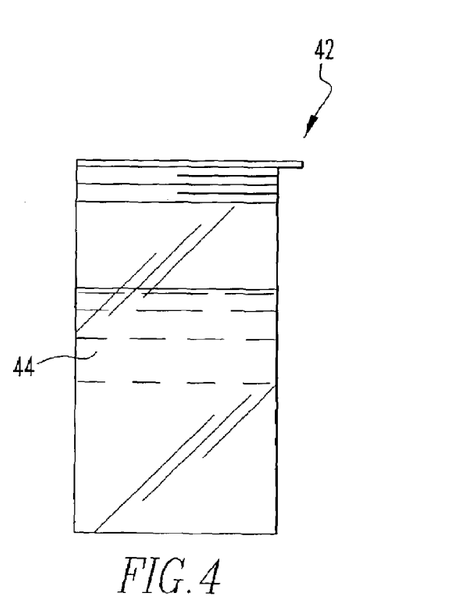
FIG. 4 is a front elevational view of the second vial section with protective foil cover of the kit of the present invention.
Figure 5:
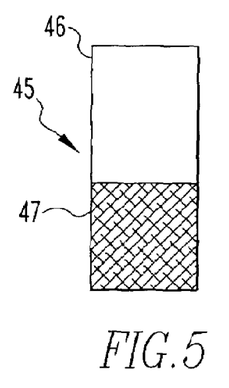
FIG. 5 is a front elevational view of the indicator strip section of the kit of the present invention.
Figure 6:
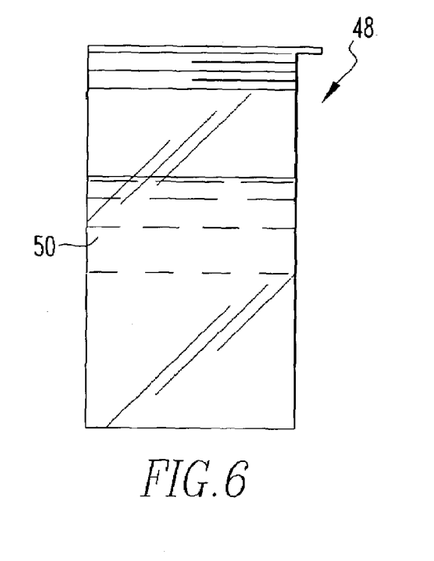
FIG. 6 is a front elevational view of the preferred embodiment of the third vial section of the kit of the present invention.
Figure 7:
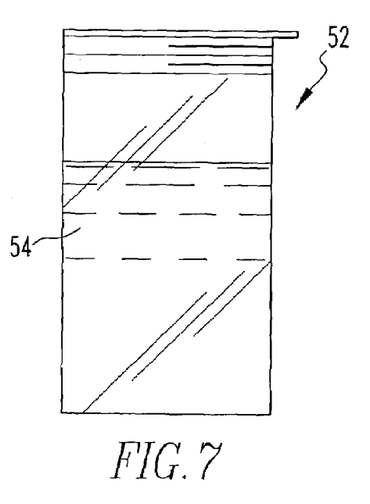
FIG. 7 is a front elevational view of the fourth vial section of the kit of the present invention.

The kit of the present invention also includes a swab which is shown in FIG. 3 generally at numeral 36. This swab 36 includes a stick 38 with a break point 39, a handle 40 and an absorbent cotton section 41. Also included in the kit of the present invention is a second vial shown generally in numeral 42 in FIG. 4 which is essentially identical in structure to vial 22 except that it contains a reporter hormone solution 44 rather than the buffer solution 34. The kit of the present invention also includes a strip 45 which is shown in FIG. 5. The strip 45 has a grip end 46 and a color end 47. The function and operation of this strip is described hereafter. The kit also includes a third vial 48 which is essentially to vial 24 except that it contains a liquid wash solution 50 rather than the buffer solution 34. Finally, the kit includes a fourth vial shown generally at numeral 52 in FIG. 7 which is also essentially identical to the first vial 22 except that it contains a reporter solution 54 instead of the buffer solution 34.

The reporter solution is a compound that, when reacted with the reporter hormone/enzyme, changes color. The assay can be optimized so that the color can either be seen on the spot on the cap or in the vial solution. It is one of the substrates of the enzyme portion of the reporter hormone complex. Non-limiting examples include 3,3',5,5'-tetramethylbenzidine for use with horseradish peroxidase reporter enzyme; p-nitrophenylphosphate with alkaline phosphatase reporter and -nitrophenyl-D-galactopyranoside (ONPG) with galctosidase.

Figure 8A:
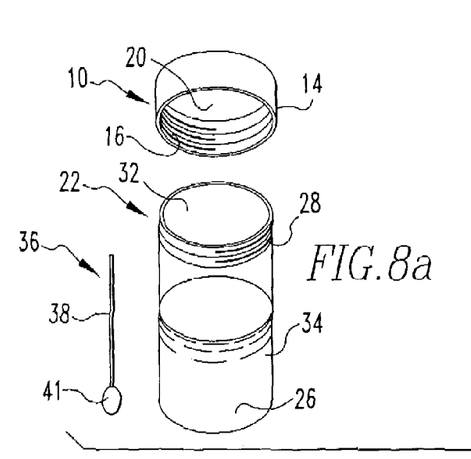
FIGS. 8a, 8b, and 8c are successive perspective views of the first vial section, the solid phase antibody cap section, and the swab section in which the first step of a preferred embodiment of the method of the present invention is illustrated.
Figure 8B:
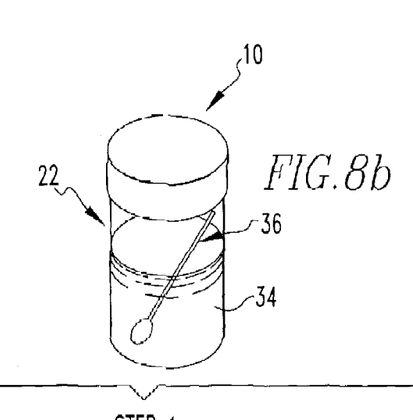
Figure 8C:
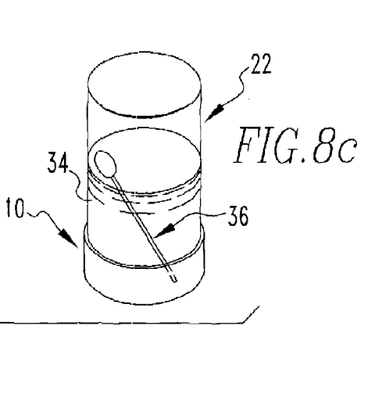

Referring to FIGS. 8a-11c, the method of this invention is illustrated. The first step in this method is illustrated with particular reference to FIGS. 8a-8c. In FIG. 8a the first vial or vessel 22 with the foil protective cover 30 removed is collected with the cap 10 and the swab 36. The swab is then saturated with saliva from a mare and is then inserted through the open top 32 into the buffer solution 34 in the first vial 22. Referring particularly to FIG. 8b, the cap 10 is then positioned over the open end 32 of the first vial 22 and attached thereto by the mating screw threads 16 and 28. Referring to FIG. 8c, the first vial 22 is then inverted so that the buffer solution 34 and the inner solid phase antibody layer 20 are in contact.

It is in this step that the equine hormone binds to the antibodies. After a fixed time the first vial 22 is stood upright and the cap with the tightly bound hormones are removed. In order for this test to be sensitive to the amount of hormone present in the saliva so as to represent various stages of gestation or the sex of the animal, the amount of antibody that is chemically attached to the cap will have been titrated empirically for each antibody, reporter hormone, and species. Therefore, after step one, the amount of antibodies that are not bound up with hormone will be the greatest or those mares that are most removed from complete gestation.

Figure 9A:
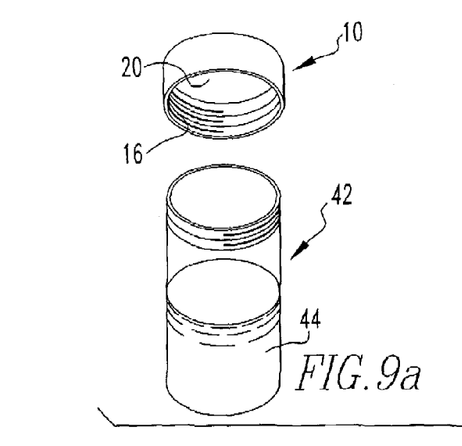
FIGS. 9a, 9b, and 9c are successive perspective views of the second vial, the solid phase antibody cap, and the strip in which the second step of the preferred embodiment method of the present invention is illustrated.
Figure 9B:
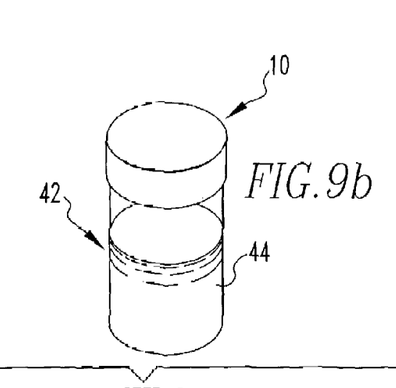
Figure 9C:
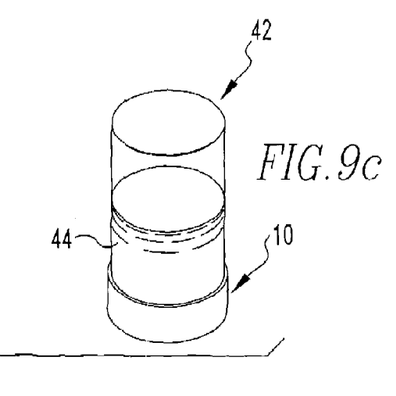

Referring to FIGS. 9a-9c, the second step in the method is shown. Referring particularly to FIG. 9a, the cap 10 is removed adjacent to the second vial or vessel 42 which contains the reporter hormone solution 44. The cap 10 is then emplaced on the second vial 42 as is shown in FIG. 9b. The second vial 42 is then inverted so that the reporter hormone solution 44 is in contact with the solid phase antibody layer 20 on the inner side of the top section of the cap 10. The reporter hormone fills up any remaining antibodies left from the first step. The number of reporter hormones, therefore, on the cap at the end of this step is greatest for saliva with the least hormone, and is the least for saliva with the maximum hormones.

Figure 10A:
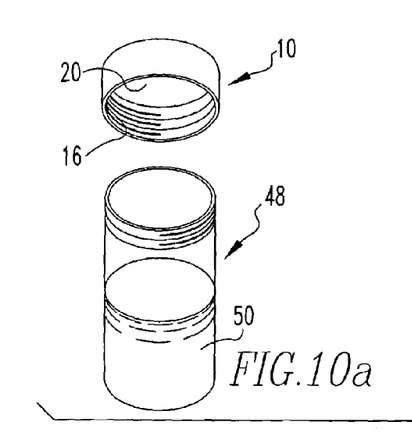
FIGS. 10a, 10b, and 10c are each perspective views of the third vial, the solid phase antibody cap, and the indicator strip in which the third step of the preferred embodiment of the present invention is illustrated.
Figure 10B:
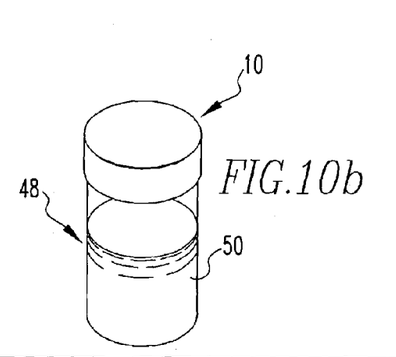
Figure 10C:
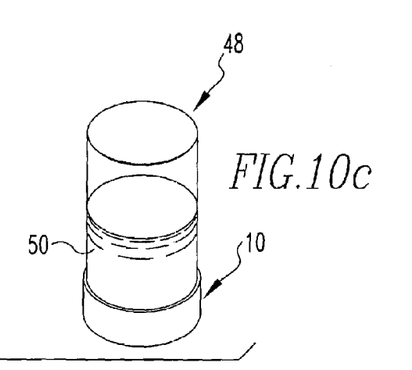

Referring to FIGS. 10a-10c, the third step in the method of this invention is illustrated. Referring particularly to FIG. 10a, the cap 10 is moved adjacent the third vial or vessel 48 which is partially filled with the washing solution 50. As is shown in FIG. 10b, the cap 10 is then emplaced on the third vial 48. As is shown in FIG. 10c, the third vial 48 is then inverted to place the solid phase antibody layer 20 on the inner side of top 12 of cap 10 in contact with the wash solution 50 to remove any unwanted materials from the solid phase antibody layer 20 that may have originated from the saliva or the reporter solution 44.

Figure 11A:
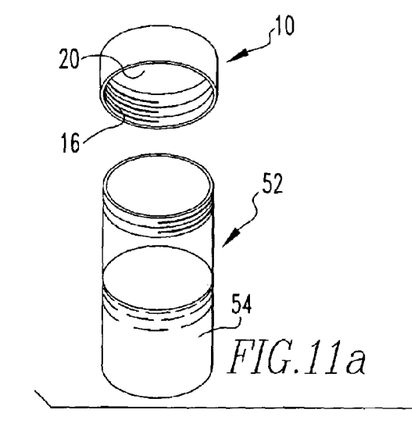
FIGS. 11a, 11b, and 11c are successive perspective views of the fourth vial, the solid phase antibody cap, and the indicator strip illustrating fourth step in the preferred embodiment of the present invention.
Figure 11B:
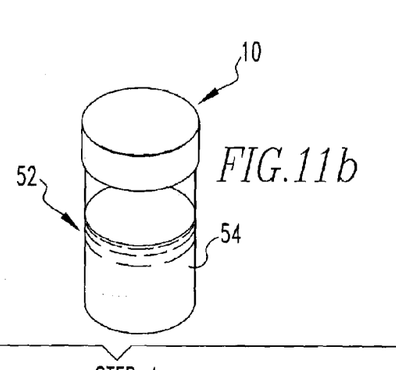
Figure 11C:
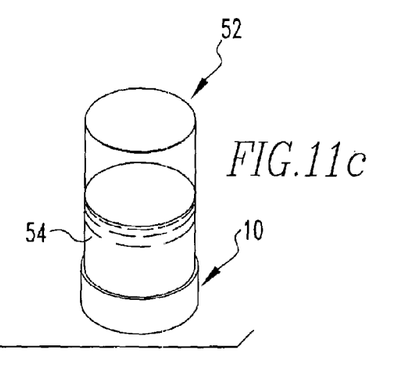
Figure 12A:
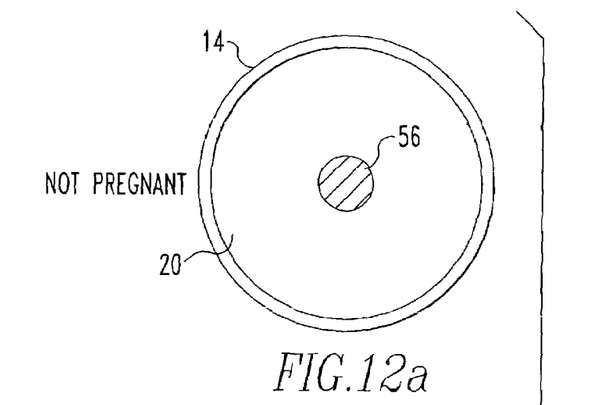
FIGS. 12a, 12b and 12c are plan views of the vial tap and indicating strip illustrating fifth step of the present invention.
Figure 12B:
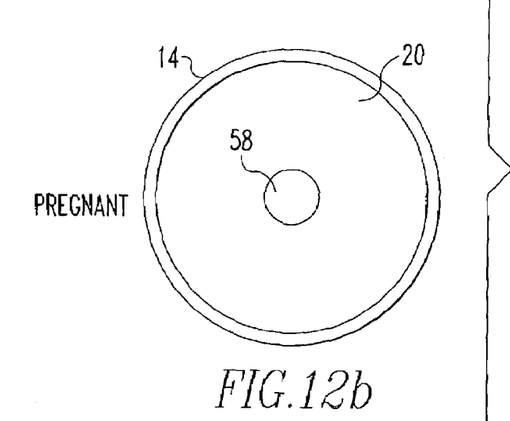
Figure 12C:
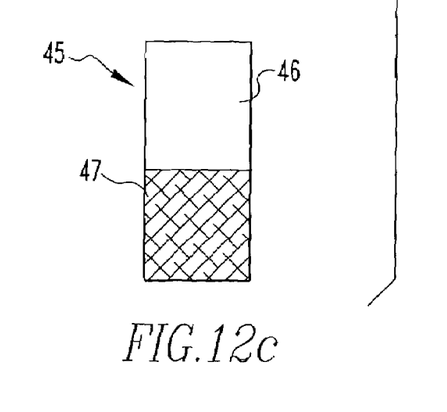
Figure 13:
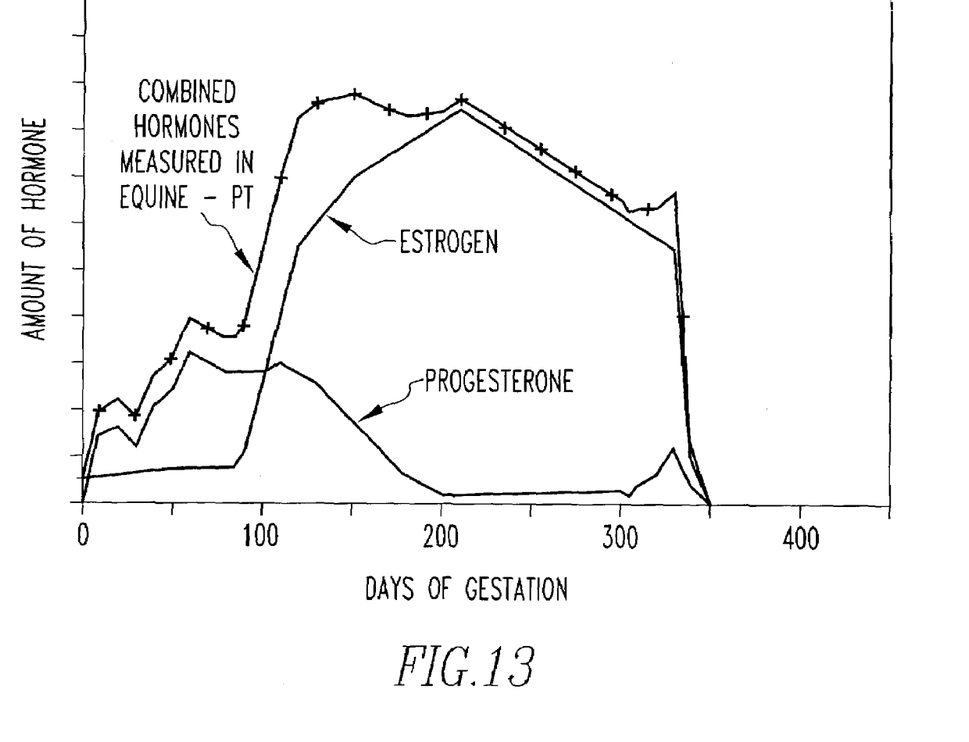
FIG. 13 is a graph showing equine levels of progesterone in saliva at various stages of pregnancy.

Referring to FIGS. 11a-11c, the cap 10 is removed from the third vial 48 to a position adjacent the fourth vial or vessel 52 which contains color solution 54. The cap 10 is then inserted onto the fourth vial 52, and the fourth vial 52 is inverted to place the color solution 54 into contact with the solid phase antibody layer 20. The intensity of the color of the color solution 54 will depend on the amount of reporter hormone that was bound to the solid phase antibody layer 20 while the cap 10 was attached to the second vial 42 in the second step of this method.

In the final step of the procedure, the color solution 54 in the fourth vial 52 is compared with a color control strip or other indicator of a positive hormone presence such as strip 45. The amount of color is proportional to the amount of reporter hormone which is dependent on the amount of hormone in the original saliva sample. The intensity of the color solution 54 in fourth vial 52 is therefor, an indicator of the gestational state or the sex of the animal.

EXAMPLE 1

A kit is prepared as described according to the foregoing. Supplies and chemicals include a 0.1 M citrate buffer, pH 5.0 with preservative, anti-progesterone antibody in a neutral buffer solution, nitrocellulose paper, kit components as described in the figures, color solution with o-phenylenediamine with 0.012% $H_2O_2$, detergent/surfactant as described above which is a commercially available reporter hormone for example, a commercially available progesterone conjugated to horseradish peroxidase.

1. Preparation of the Active Removable Surface (Cap):

The active surface is commercially available nitrocellulose paper (NCP). NCP irreveribly binds proteins with high affinity. Antibody is applied to the NCP as described below in (2). NCP is cut to fit inside the Cap and is attached, possibly with adhesive, a snap in ring, or other means that do not interfere with observing the antibody spot when color occurs. The resulting cap is the Active Cap.

2. Preparation of the Antibody Spot on the NCP:

A commercially available antibody to progesterone is diluted to a predetermined level wherein multiple applications of sub-microliter volumes can be applied to the NCP to get a sharp, small spot for ultimate viewing of the color development. The antibody is applied to the NCP, let the spot dry, and re-apply the antibody. This procedure is repeated until the pre-determined amount of antibody is absorbed to the NCP. The correct amount of antibody attached to NCP will be that amount that gives the best differential between saliva of mares that are pregnant or not. This is determined experimentally using multiple saliva samples from different pregnant mares and mares who are not pregnant (or male horses) and empirical observations of hormone binding and reporter hormone binding and maximum sensitivity.

3. Preparation of Reporter Hormone Solution:

Progesterone-horseradish peroxidase reporter hormone can be purchased or manufactured. The reporter is diluted in citrate buffer. The dilution factor depends on the initial concentration of reporter and is determined experimentally by determining the amount of reporter that gives the maximum distinction between pregnant and non-pregnant horses with a specific lot of antibody spot on NCP. Minimum concentrations that give adequate signal are preferred.

4. Preparation of the Reporter Solution: approximately 34 mg of o-phenylenediamine is dissolved in 100 ml of 0.1 M citrate buffer at pH 5.0, containing 0.012% $H_2O_2$. Preservatives and surfactants can be added to a final concentration of less than approximately 0.1% to inhibit non-specific binding of either the colorless reporter or its colored reacted species.

5. Buffer:

The buffer for this assay will be Tris buffer, pH 7.4 with 0.1% TWEEN 20 and 0.1% bovine serum albumin as a stabilizer and is used in all steps except the final color reaction.

6. Preparing the Kit:

The vials are standard 40 ml screw cap glass vials with TEFLON-lined caps. There are four separate vials that will be used during the assay and are called Vial 1, Vial 2, Vial 3, and vial 4 based on the sequence in which they are used. Each vial has it's own cap. Only Vial 1 has an active cap and it will be transferred to each of the vials as the assay proceeds. As the Vial 1 cap is removed from Vial 1 and put on Vial 2, the cap from Vial 2 will be put on Vial 1 for safe disposal of Vial 1. As Vial 1 cap is removed from Vial 2 and put onto Vial 3 during the assay described below, the cap from Vial 3 will be put on Vial 2 for safe disposal of Vial 7. This Procedure Continues for all Four Vials:

Vial 1 contains 30 ml buffer. Vial 2 contains 30 ml of Reporter Hormone in buffer. Vial 3 contained 40 ml of buffer. Vial 4 contains 30 ml of Reporter Solution.

The pregnancy of the mare is determined as follows:

The approximately 10 inch cotton swab is put into the mare's mouth and run around various parts of the mouth until the cotton is thoroughly moistened with saliva. The swab is then scored (or it can be scored in advance or purchased scored) at approximately 1 inch length so that the portion containing the cotton can be broken off and placed into vial 1 and the lid tightened. Vial 1 is inverted, the cotton should still be submersed in the buffer, and the cap on vial 1 is in contact with the buffer. These components are incubated for approximately 30 minutes wherein the mare's hormones in the saliva bind to the antibody on the Active Cap.

The active cap is removed from vial 1 and put onto vial 2 containing the reported hormone solution. Vial 2 is inverted to contact the active cap with the reporter hormone solution. These components are incubated for approximately 30 minutes. All remaining antibody binding sites are bound to the reporter hormone.

The active cap is removed from vial 2 and put onto vial 3 containing the buffer used as a wash solution to remove excess reporter hormone. Vial 3 is inverted to contact the active cap with the buffer. The vial can be gently shaken to facilitate the washing process. These components are incubated for approximately 30 minutes. This substrate will precipitate on the Active Cap during the formation of the colored enzyme product. By using alternate commercially available substrates as indicator solutions, the colored product of the enzyme reaction can be found in the solution instead of the Active Cap, and the indicator of pregnancy is the intensity of the color of the solution in Vial 4. This can be compared to a supplied color strip where the pregnancy cut-off level is indicated.

The active cap is removed from vial 3 and put onto vial 4 containing the reporter solution. Vial 4 is inverted to contact the active cap with the reporter solution. These components are incubated for approximately 30 minutes.

The active cap is removed from vial 4. The color spot on the active cap is compared to the color strip provided. If the color spot is lighter than the "pregnant" indicator on the color strip, then the mare is pregnant.

EXAMPLE 2

Example 1 can be performed on a semi-rigid material with properties similar to the active cap. The semi-rigid material can be manufactured in the shape of a strip or stick. This active strip will have the anti-progesterone antibody coated on it. Instead of have an active cap for color development, the active strip will be the indicator or pregnancy and will be moved from Vial 1 to Vial 4, instead of the Active Cap in Example 1. In this example, the steps occur as in Example 1 except that the vials need not be inverted. As in Example 1, alternate color production schemes may be used that would result in color development in solution instead of on the active surface of the strip or stick.

Beside progesterone as an equine pregnancy indicator, there are other hormone indicators for equine species. In addition, all mammals have small peptide hormones that change on the state of pregnancy. Those skilled in the art will appreciate that it will be possible to make use of such alternate hormones in the practice of the method and device of this invention.

It will also be appreciated by those skilled in the art that the method and apparatus described herein may be adapted for identification of the sex of various avians and other animals without readily identifiable sex characteristics.

It will be appreciated that a method for detecting pregnancies in mammals and for identifying sex in monomophic avians and other animals and a kit for use therein, has been described, which method is easy to do, is inexpensive, and may be performed at home without expensive laboratory facilities or specialized training. This method and kit also eliminate any complicated measuring or manipulation requirements for the user.

Accordingly, the improved PREGNANCY AND SEX IDENTIFICATION TEST BASED ON SALIVA OR OTHER BODILY FLUIDS method apparatus is simplified, provides an effective, safe, inexpensive, and efficient method and device which achieves the enumerated objectives, provides for eliminating difficulties encountered with prior methods and devices, and solves problems and obtains new results in the art.

In the foregoing description, certain terms have been used for brevity, clearness, and understanding; but no unnecessary limitations are to be implied therefrom beyond the requirement of the prior art, because such terms are used for descriptive purposes and are intended to be broadly construed. Moreover, the description and illustration of the invention is by way of example, and the scope of the invention is not limited to the exact details shown or described.

Having now described the features, discoveries, and principles of the invention, the manner in which the PREGNANCY AND SEX IDENTIFICATION TEST BASED ON SALIVA OR OTHER BODILY FLUIDS is constructed and used, the characteristics of the construction, and the advantageous new and useful results obtained; the new and useful structures, devices, elements, arrangements, parts, and combinations are set forth in the appended claims.

The invention claimed is:

1. A method of testing a female animal for pregnancy, the method comprising the steps of:
    (a) providing a first liquid medium and then introducing a bodily fluid containing a hormone from the animal into said first liquid medium to provide a first liquid mixture contained in a first vessel having an opening and a removable cap adapted to close said opening, wherein said cap has an entirely substantially flat solid inner surface with antibodies attached thereto and contacting said first liquid mixture with the solid inner surface to provide a reaction wherein said hormone of said bodily fluid binds with at least some of said antibodies attached to said solid inner surface;
    (b) providing a reporter hormone solution containing a reporter hormone contained within a second vessel having an opening and adapted for receiving and being closed by said removable cap such that, upon placing said entirely substantially flat solid inner surface of said removable cap in contact with the reporter hormone solution, a reaction is provided wherein said reporter hormone binds with any remaining antibodies attached to said solid surface;
    (c) contacting the entirely substantially flat solid inner surface with an indicating solution; and
    (d) then making a determination regarding pregnancy of the animal based on a change in color of either the solid inner surface or the indicating solution.

2. The method of claim 1 wherein between steps (b) and (c) there is added the additional step (e) of washing the solid inner surface.

3. The method of claim 1 wherein, in step (c), the indicating solution causes a change of color in the solid inner surface, and, in step (d), the determination regarding pregnancy is based on the color of the solid inner surface.

4. The method of claim 1 wherein in step (c) there is a change in the color of the indicating solution itself, and in step (d) the determination regarding pregnancy is based on the color of the indicating solution.

5. The method of claim 3 wherein, in step (d), a visual comparison means denoting the original color of the solid inner surface is provided in determining the change of color of the solid inner surface.

6. The method of claim 4 wherein in step (d) a visual comparison means denoting the original color of the indicating solution is provided in determining the change of color of the indicating solution.

7. The method of claim 1 wherein in step (a) the first liquid medium is a buffer liquid.

8. The method of claim 7 wherein the buffer liquid is selected from the group consisting of any buffer in which the antibodies, hormone of said bodily fluid and solid phase are stable.

9. The method of claim 1 wherein the bodily fluid is selected from the group consisting of blood, plasma, urine, milk and saliva.

10. The method of claim 9 wherein the bodily fluid is saliva.

11. The method of claim 1 wherein in step (a) the hormone of said bodily fluid is an indicating hormone which is related to pregnancy, and the amount of antibodies on the solid inner surface is proportional to the amount of indicating hormone which would be present at complete gestation.

12. The method of claim 11 wherein the indicating hormone is selected from the group consisting of progesterone and estrogen and hormones found in bodily fluids that are indicative of either pregnancy of the animal.

13. The method of claim 1 wherein the reporter hormone is selected from the group consisting of any compound that, when reacted with the indicating solution, change color.

14. The method of claim 12 wherein on completion of step (b) the occurrence of reporter hormone on the solid inner surface is inversely proportional to the occurrence of indicating hormone in the bodily fluid.

15. The method of claim 1 wherein in step (c) the appearance which is related to the amount of the reporter hormone contacted is a color which becomes more intense depending on the amount of reporter hormone which is contacted.

16. The method of claim 1 wherein the animal is a female mammal in the case of the pregnancy test.

17. The method of claim 10 wherein the animal is selected from the group consisting of cows and horses.

18. The method of claim 17 wherein said antibodies are antibodies against a compound selected from the group consisting of progesterone, estrogen, follicle stimulating hormone, leutinizing hormone, and derivatives and metabolites thereof.

19. The method of claim 1, wherein in step (c), said indicating solution is contained in a third vessel having an opening and adapted for receiving and being closed by said removable cap such that said indicating solution contacts said solid surface when said removable cap is placed on said third vessel.

20. The method of claim 1, wherein contacting said first liquid mixture of step (a) with the solid inner surface to provide a reaction is accomplished by inverting the first vessel.

21. The method of claim 1, wherein the reporter hormone solution of step (b) is brought into contact with the solid inner surface by inverting the second vessel.

22. The method of claim 2, wherein the washing solution of step (e) is brought into contact with the solid inner surface by inverting the vessel.

23. The method of claim 1, wherein the indicating solution of step (c) is brought into contact with the solid inner surface by inverting the vessel.

* * * * *